US00PP17892P2

(12) United States Plant Patent
Hall

(10) Patent No.: US PP17,892 P2
(45) Date of Patent: Aug. 7, 2007

(54) *LAVANDULA* PLANT NAMED 'GRACE LEIGH'

(50) Latin Name: *Lavandula angustifolias*
Varietal Denomination: Grace Leigh

(76) Inventor: Elsie Hall, Leighvander, RD 1, Wairau Valley, Marlborough (NZ)

( * ) Notice: Subject to any disclaimer, the term of this patent is extended or adjusted under 35 U.S.C. 154(b) by 259 days.

(21) Appl. No.: 11/216,138

(22) Filed: Aug. 31, 2005

(51) Int. Cl.
*A01H 5/00* (2006.01)

(52) U.S. Cl. ..... Plt./226

(58) Field of Classification Search ..... Plt./226
See application file for complete search history.

(56) References Cited

PUBLICATIONS

UPOV ROM GTITM Computer Database, GTI Jouve Retrieval Software 2005/05 Citation for 'Grace Leigh'.*

* cited by examiner

*Primary Examiner*—Wendy Haas

(57) ABSTRACT

A new cultivar of *Lavendula* plant named 'Grace Leigh' that is characterized by silver spike flower heads with a violet corolla, an arching habit and fragrant silver grey green leaves.

1 Drawing Sheet

Botanical classification: *Lavendula angustifolias.*
Variety denomination: 'Grace Leigh'.

BACKGROUND OF THE INVENTION

The present invention relates to a new and distinct cultivar of *Lavendula angustifolia* and hereinafter referred to by the cultivar name 'Grace Leigh'. The new cultivar was discovered growing in a cultivar area of Wairau Valley, Marlborough, New Zealand in 1999. The exact parents are unknown.

The new Lavender plant 'Grace Leigh' is distinct and unique due to its silver white flower heads, violet corolla, fragrant silver grey green leaves and arching foliage.

The closest comparison plant is *Lavendula* 'Alba' (not patented). 'Grace Leigh' is distinguishable from 'Alba' by its violet corolla, arching habit and fragrant leaves.

The new cultivar was first asexually propagated by cuttings in Wairau Valley, Marlborough, New Zealand by the inventor in 1999. Since that time, under careful observation, the unique characteristics of the new cultivar have been uniform, stable and reproduced true to type in successive generations of asexual reproduction.

SUMMARY OF THE INVENTION

The new lavender 'Grace Leigh' is distinguished from other known varieties of *Lavendula,* by the following characteristics:

1. Silver grey green leaves.
2. Silver white flower heads with a violet corolla.
3. Strong scent.

These unique traits set 'Grace Leigh' apart from other existing varieties known to the inventor.

'Grace Leigh' is distinguishable from *Lavendula* 'Alba', by foliage, flower color and fragrance.

BRIEF DESCRIPTION OF THE DRAWINGS

The accompanying color photograph illustrates the distinguishing characteristics of the new cultivar 'Grace Leigh' and shows an overall view of a 3 month old plant. All photographs are taken using conventional photographic techniques and although foliage colors may appear different from actual colors due to light reflectance, they are as accurate as possible by conventional photography.

BOTANICAL DESCRIPTION OF THE PLANT

The following is a detailed description of the *Lavendula* cultivar named 'Grace Leigh'. Date was collected in Wairau Valley, Marlborough, New Zealand from 3 month old plants. The plants were grown outdoors under natural conditions. The time of year was March. The temperature ranged from 12 to 30 degrees centigrade during the day and from 5 to 18 degrees centigrade at night. No growth retardant was used. Phenotypic differences may be observed with variations in environmental, climatic, and cultural conditions, without however, any difference in genotype. Color determinations are in accordance with the 1995 Royal Horticultural Society Color Chart except where general color terms of ordinary dictionary significance are used. The growing requirements are similar to the species and no disease problems have been observed.

Botanical classification: *Lavandula angustifolia* 'Grace Leigh'.
Common name: Lavender.
Parentage: The parents of 'Grace Leigh' are unknown.
Type: Aromatic perennial shrub.
Use: Ornamental and oil producing plant.
Growth rate: 20 cm. per month.
Habit: Bushy, arching when mature.
Height: 60 cm. in height.
Spread: 90 cm. in width.
Hardiness: USDA zone 5 to zone 10.
Propagation method: Cuttings.

Vigor: Average medium grower.
Root system: Fine and fibrous.
Soil: Plant in well-drained soil.
Light levels: Plant in full sun.
Special needs: None observed.
Time to initiate roots: 6 weeks from an unrooted cutting during the summer.
Time to produce a rooted cutting: 4 weeks during the summer.
Branching habit: Erect, upright, semi-open, arching when mature.
Pinching: No.
Internode length: 3 cm.
Stem:
*Shape.*—Cylindrical.
*Surface.*—Puberulent.
*Color.*—146A.
*Size.*—Average 0.5 to 2 mm. in diameter, 22 cm. in length.
*Strength.*—Strong.
Foliage:
*Arrangement.*—Erect stems of basal leaves, mature leaves, slightly glossy.
*Leaf dimensions.*—2 to 3 cm. in length and 2 to 4 mm. in diameter.
*Leaf division.*—Simple.
*Apex.*—Acute.
*Base.*—Attenuate.
*Margins.*—Entire.
*Leaf shape.*—Linear.
*Color of mature leaves* (*upper and lower surfaces*).—146A.
*Color of young leaves* (*upper and lower surfaces*).—214A.
*Upper and lower surfaces.*—Puberulent.
*Foliage fragrance.*—Strong scent.
*Petiole.*—Sessile.
*Length.*—4 cm. in length.
*Width.*—2 to 4 mm. in width.
Flower:
*Flowering habit.*—Early to mid summer, flowers summer continuously.
*Type of inflorescence.*—Terminal spike.
*Shape of inflorescence.*—Cylindrical-conical.
*Spike size.*—2 to 4 cm. in height and 6 to 10 mm. in width.
*Flower shape.*—Cylindric, dense, apices blunt.
*Flower size.*—2 to 3.5 mm. in length and 0.5 to 2 mm. in diameter.
*Flower shape.*—5 lipped.
*Corolla color.*—86D.
*Calyx shape.*—Tubular.
*Calyx color.*—193A.
*Calyx surface.*—Pubescent.
*Bracts.*—Sterile bracts.
*Bract shape.*—Broad.
*Bract dimensions.*—0.5 to 2 mm. in length and 0.5 to 1 mm. in width.
*Bract color.*—193A.
*Flower longevity.*—21 to 25 days.
*Flower longevity as a cut flower.*—7 days.
Peduncle:
*Peduncle length.*—25 cm.
*Peduncle diameter.*—0.5 to 1 mm.
*Peduncle strength.*—Strong.
*Peduncle color.*—146A.
Reproductive organs: Have not been observed.
Seed production: Has not been observed.
Disease and pest resistance: Has not been observed.

It is claimed:

1. A new and distinct variety of *Lavendula* plant named 'Grace Leigh' as described and illustrated.

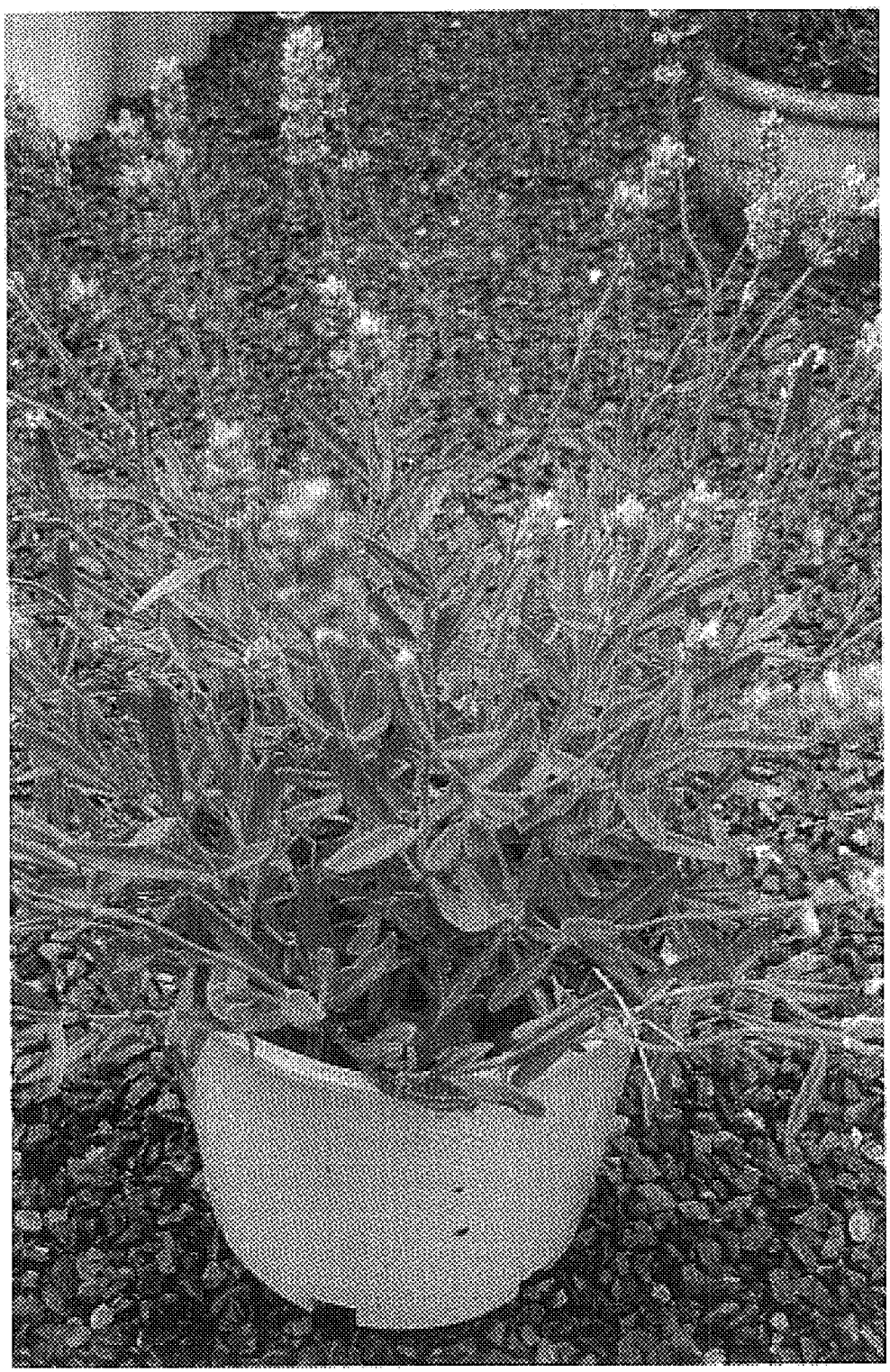

* * * * *